United States Patent [19]

Yoshikuni et al.

[11] Patent Number: 4,831,055
[45] Date of Patent: May 16, 1989

[54] BENZOIC ACID DERIVATIVES

[75] Inventors: Yoshiaki Yoshikuni, Uji; Shoichi Chokai, Kameoka; Takayuki Ozaki, Moriyama; Hirotsugu Yoshida, Kyoto; Haruo Tanaka, Hikone; Jun Segawa, Kyoto, all of Japan

[73] Assignee: Nippon Shinyaku Co., Ltd., Japan

[21] Appl. No.: 59,057

[22] Filed: Jun. 8, 1987

[30] Foreign Application Priority Data

Jun. 11, 1986 [JP] Japan ................... 61-136407
Jul. 1, 1986 [JP] Japan ................... 61-155736

[51] Int. Cl.$^4$ ............... A61K 31/165; C07C 103/22
[52] U.S. Cl. .............................. 514/539; 548/478; 514/563; 560/42; 562/451
[58] Field of Search .................. 560/42; 562/451; 514/539, 563

[56] References Cited

U.S. PATENT DOCUMENTS

| | | | |
|---|---|---|---|
| 2,872,476 | 2/1959 | Melkonian et al. | 560/42 |
| 2,927,132 | 3/1960 | Barber et al. | 564/185 |
| 4,182,775 | 1/1980 | Weyer et al. | 562/451 X |
| 4,298,603 | 11/1981 | Chang et al. | 560/42 X |
| 4,409,240 | 10/1983 | Takita et al. | 514/539 X |
| 4,418,069 | 11/1983 | Welter et al. | 564/185 X |

OTHER PUBLICATIONS

Dermer et al., "Ethylenimine and Other Aziridines", (1969); pp. 256–261; Academic Press, N.Y.
Abstract of Article to Gutniak et al., in Acta Endocrinol., 100, Suppl. 247, 26 (1982).

Primary Examiner—Joseph Paul Brust
Attorney, Agent, or Firm—Jacobs & Jacobs

[57] ABSTRACT

Compounds of formula (I)

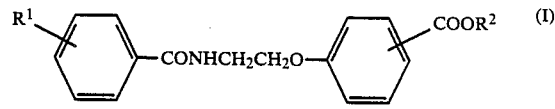

or a pharmaceutically acceptable salt thereof, wherein $R^1$ is hydrogen, halogen or alkyl and $R^2$ is hydrogen or alkyl are useful to reduce serum lipids in animals, including humans.

9 Claims, No Drawings

BENZOIC ACID DERIVATIVES

The present invention relates to benzoic acid derivatives. In particular, the present invention provides compounds of formula I

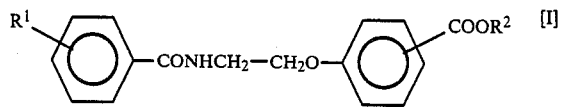

and pharmaceutically acceptable salts thereof, wherein $R^1$ is hydrogen, halogen or alkyl and $R^2$ is hydrogen or alkyl. Compounds (I) reduce serum lipids, such as serum cholesterol, and are thus useful in the treatment and prevention of hyperlipemia and arteriosclerosis.

Benzoic acid derivatives are known. Acta Endocrinol., 100, Suppl. 247, 26 (1982), proposes a benzoic acid derivative as an agent in the treatment of diabetes mellitus. However, compounds (I) of the present invention and their use to reduce serum lipids are novel.

When $R^1$ and $R^2$ are alkyl, it is suitable that the alkyl may be straight or branched chain alkyl of from about 1 to about 7 carbon atoms, such as methyl, ethyl, n-propyl, isopropyl, n-butyl, isobutyl, tert-butyl, n-pentyl, isopentyl, n-hexyl, isohexyl, n-heptyl, isoheptyl, and the like. Alkyl of from about 1 to about 4 carbon atoms is preferred.

When $R^1$ is halogen, it may suitably be fluorine, chlorine, bromine or iodine.

Compound (I) may be used as the free acid or as a pharmaceutically acceptable salt thereof, such as the sodium salt or calcium salt or the like.

In addition to the compounds as referred to in the Examples given later, the following compounds may be listed as representative compounds of the invention.

4-[2-(3-Methylbenzamido)ethoxy]benzoic acid;
Methyl 4-[2-(2-methylbenzamido)ethoxy]benzoate;
Methyl 4-[2-(3-isopropylbenzamido)ethoxy]benzoate;
Ethyl 4-[2-(2-isopropylbenzamid)ethoxy]benzoate;
4-[2-(3-Isopropylbenzamido)ethoxy]benzoic acid;
Sodium 4-[2-(2-isopropylbenzamido)ethoxy]benzoate;
4-[2-(3-tert-Butylbenzamido)ethoxy]benzoic acid;
Sodium 4-[2-(2-tert-butylbenzamido)ethoxy]benzoate;
3-[2-(Benzamido)ethoxy]benzoic acid;
Ethyl 3-[2-(3-methylbenzamido)ethoxy]benzoate;
3-[2-(3-Isopropylbenzamido)ethoxy]benzoic acid;
3-[2-(3-tert-Butylbenzamido)ethoxy]benzoic acid;
Sodium 2-[2-(benzamido)ethoxy]benzoate;
2-[2-(2-Methylbenzamido)ethoxy]benzoic acid;
Sodium 2-[2-(3-isopropylbenzamido)ethoxy]benzoate;
Methyl 2-[2-(2-tert-butylbenzamido)ethoxy]benzoate;
Methyl 4-[2-(3-chlorobenzamido)ethoxy]benzoate;
Ehtyl 4-[2-(2-chlorobenzamido)ethoxy]benzoate;
4-[2-(3-Chlorobenzamido)ethoxy]benzoic acid;
Sodium 4-[2-(2-chlorobenzamido)ethoxy]benzoate;
Methyl 4-[2-(3-fluorobenzamido)ethoxy]benzoate;
4-[2-(2-Fluorobenzamido)ethoxy]benzoic acid;
Methyl 4-[2-(3-bromobenzamido)ethoxy]benzoate;
4-[2-(2-Bromobenzamido)ethoxy]benzoic acid;
Methyl 3-[2-(2-chlorobenzamido)ethoxy]benzoate;
3-[2-(3-Fluorobenzamido)ethoxy]benzoic acid;
Ethyl 3-[2-(2-bromobenzamido)ethoxy]benzoate;
2-[2-(3-Chlorobenzamido)ethoxy]benzoic acid;
Ethyl 2-[2-(2-fluorobenzamido)ethoxy]benzoate; and
2-[2-(3-Bromobenzamido)ethoxy]benzoic acid.

All of the compounds of the present invention (I) are novel and have not been disclosed in the prior art. They may be prepared as follows:

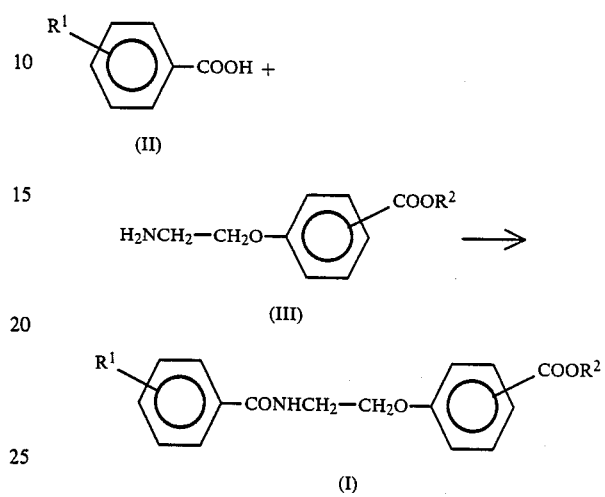

wherein $R^1$ and $R^2$ are defined above.

Thus, compound (III) is reacted with a carboxylic acid (II) or reactive derivative thereof to give (I). This acylation reaction can be carried out in a manner known per se. For example, (II) or a reactive derivative thereof can be directly combined with (III) using a condensation agent. Suitable reactive derivatives of (II) include an acid halide, imidazolide or mixed acid anhydride thereof.

Thus, when an acid halide of (II), such as an acid chloride or acid bromide, is used, the reaction is usually conducted in a suitable solvent, such as an ether type solvent, such as ethylether, tetrahydrofuran, dioxane, etc., a halogenated hydrocarbon type solvent, such as methylene chloride, chloroform, etc., a hydrocarbon type solvent, such as benzene, toluene, xylene, etc., water, or a mixture thereof, in the presence of a base, such as an inorganic base, such as potassium carbonate, sodium hydroxide, potassium hydroxide, etc., or an organic base, such as pyridine, triethylamine, etc., at $-20°$ to $+30°$ C. The amount of the acid halide is generally 1 to 1.2 moles per mole of compound (III).

When a mixed acid anhydride is used, (II) is first reacted with an alkyl chlorocarbonate (e.g. methyl chlorocarbonate, ethyl chlorocarbonate, isobutyl chlorocarbonate, etc.) in the presence of a base (e.g. an organic base, such as pyridine, triethylamine, etc.) in a suitable solvent (preferably a halogenated hydrocarbon type solvent, such as methylene chloride or chloroform) at $-20°$ to $+20°$ C. to give a mixed acid anhydride solution, which is then reacted with (III) at $-10°$ to $30°$ C. The amount of the mixed acid anhydride is preferably 1 to 1.2 moles per mole of compound (III).

When a direct condensation of (II) and (III) using a condensation agent is conducted, the reaction is generally conducted in a suitable solvent (e.g. a halogenated hydrocarbon type solvent, such as methylene chloride, chloroform, etc., an ether type solvent, such as tetrahydrofuran, dioxane, etc., or an aprotic solvent, such as acetonitrile, N,N-dimethylformamide, etc.) using a condensation agent (e.g. N,N'-dicyclohexylcarbodiimide, diphenylphosphoric acid azide, etc.) at −10° C. to room temperature. The amount of compound (II) is preferably 1 to 1.2 moles per mole of compound (III).

The starting material (III) used in the present invention is a known compound and can be manufactured by a known method such as described in Japanese published application No. 50/123671 or may be prepared as follows:

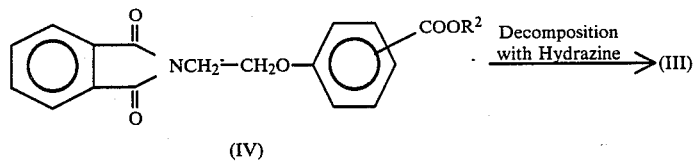

wherein $R^2$ is as defined above. Thus, the compound (IV) is refluxed in an alcohol of the formula $R^2OH$ with 1 to about 5 moles of hydrazine per mole of (IV). The compound (IV) is novel and can be manufactured by method A or B below:

(METHOD A)

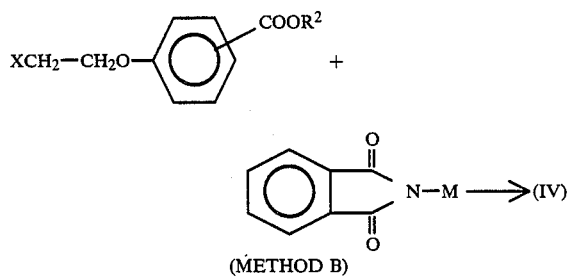

(METHOD B)

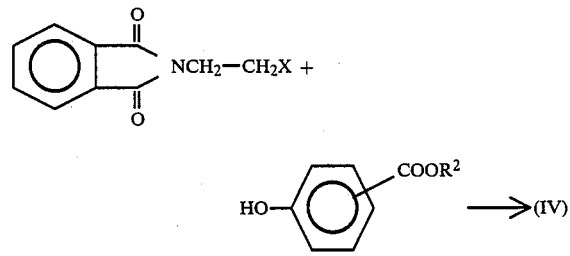

wherein M is an alkali metal, preferably potassium, X is halogen, preferably bromine, and $R^2$ is as defined above.

Method A can be conducted at 50° to 100° C. in a suitable solvent (e.g. acetonitrile, N,N-dimethylformamide, etc.) with an equimolar amount of alkali metal phthalimide.

Method B can be conducted at 40 to 100° C. in the presence of a suitable acid-removing agent (e.g. anhydrous potassium carbonate, sodium methoxide, sodium ethoxide, etc.) in a suitable solvent (e.g. N,N-dimethylformamide, acetonitrile, etc. in the case of anhydrous potassium carbonate; methanol etc. in the case of sodium methoxide; ethanol etc. in the case of sodium ethoxide) with an equimolar amount of the hydroxybenzoic acid or ester thereof.

Compound (III) may also be prepared as follows:

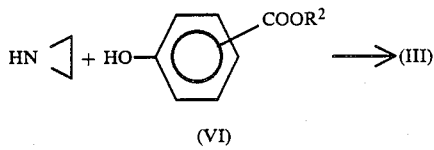

wherein $R^2$ is as defined above. Thus, (VI) is reacted with aziridine in a solvent which is usually inert to the reaction (e.g. a halogenated hydrocarbon type solvent such as methylene chloride, chloroform, etc.; an ether type solvent, such as tetrahydrofuran, dioxane, etc.; hydrocarbon type solvent such as benzene, toluene, etc.; and a nonprotonic polar solvent, such as acetonitrile, N,N-dimethylformamide, etc.) at room temperature to 120° C. to give (III). The amount of (VI) may be 1 to 3 moles per mole of aziridine.

Another method of making (III) is as follows:

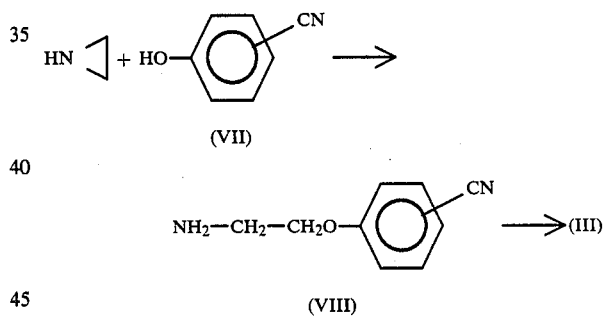

Thus, benzonitrile (VII) is made to react with aziridine to give (VIII) by the same manner as in the above reaction of aziridine and (VI). Then (VIII) is hydrolyzed with acid and esterified, if necessary, to give the desired (III). This hydrolysis reaction may be easily carried out by the use of an acid, such as hydrochloric acid, sulfuric acid, hydrobromic acid, and the like. It is preferred that the reaction is conducted in an alcohol, such as methanol, ethanol, etc. at 50° to 100° C. The amount of the acid may be 1 to 6 moles, more preferably 3 to 4 moles, per mole of (VIII).

Starting material (II) is known or can be prepared by methods analogous to known methods.

Compound (I) may also be prepared as follows:

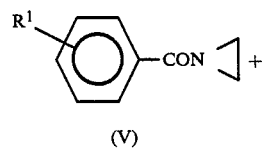

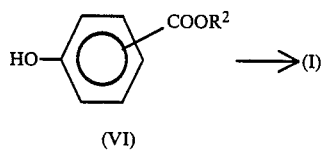

wherein $R^1$ and $R^2$ are as defined above. The reaction of compound (V) with (VI) is usually carried out in a solvent which is inert to the reaction (e.g., a halogenated hydrocarbon type solvent, such as methylene chloride, chloroform, etc.; an ether type solvent, such as tetrahydrofuran, dioxane, etc.; a hydrocarbon type solvent, such as benzene, toluene, etc.; a carbonyl type solvent, such as acetone, methyl ethyl ketone, etc.; and an alcohol type solvent such as methanol, ethanol, etc.) in the presence of a base (e.g., an inorganic base, such as potassium carbonate, sodium carbonate, sodium hydroxide, potassium hydroxide, etc.; an organic base, such as pyridine, triethylamine, etc.; and a strong base, such as sodium hydride, sodium methoxide, sodium ethoxide, potassium tert-butoxide, etc.) at room temperature to 80° C. The amount of (VI) is usually not less than one mole per mole of (V), preferably from 1 to 1.2 moles per mole of (V).

The starting material (V) may be prepared as follows:

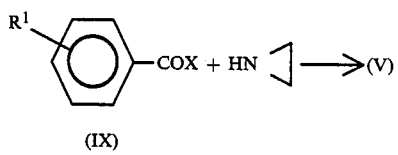

wherein $R^1$ is as defined above and X is halogen. Thus, an acid halide (IX) is reacted with aziridine in a solvent which is inert to the reaction (e.g., a halogenated hydrocarbon type solvent such as methylene chloride, chloroform, etc.; an ether type solvent, such as tetrahydrofuran, dioxane, etc.; a hydrocarbon type solvent, such as benzene, toluene, etc.; and a nonprotonic polar solvent, such as acetonitrile, N,N-dimethylformamide) in the presence of a base (e.g., an inorganic base, such as potassium carbonate, sodium, bicarbonate, sodium carbonate, sodium hydroxide, potassium hydroxide, etc.; and an organic base, such as pyridine, triethylamine, etc.) at −20° C. to room temperature to afford (V). The amount of the aziridine is not less than one mole per mole of (IX), preferably from 1.0 to 1.2 moles per mole of the acid halide (IX).

The compound (I) of the present invention in which $R^2$ is hydrogen may also be manufactured by hydrolyzing the ester (I) manufactured as hereinabove (i.e. $R^2$=lower alkyl). Such a hydrolysis reaction is carried out in the presence of a mineral acid, such as hydrochloric acid or sulfuric acid in aqueous alcohol (e.g. aqueous methanol or ethanol) at room temperature to 80° C. The amount of the acid used may be 0.1 to 10 moles, more preferably 0.2 to 3 moles, per mole of the ester ($R^2$=lower alkyl).

This hydrolysis reaction may also be conducted in the presence of potassium carbonate, sodium hydroxide, potassium hydroxide or the like in water, methanol, ethanol or a mixture thereof at, in general, 0° to 150° C. or, more preferably, at 20° to 100° C. The amount of the alkali used is 1 to 5 moles, more preferably 2 to 3 moles, per mole of the ester ($R^2$=lower alkyl).

Compound (I) wherein $R^2$ is alkyl may also be prepared by esterifying the free acid form of (I) ($R^2$ is hydrogen). Such an esterifying reaction may be conducted by an esterification technique known per se, such as with diazomethane, alcohol and acid (e.g. hydrochloric acid, sulfuric acid, p-toluene sulphonic acid, etc.) or with thionyl chloride and an alcohol.

When the compound (I) obtained hereinabove is the ester or the free acid, it may be converted to a salt thereof in a manner known per se. In the case of the alkali metal salt, for example, the ester ($R^2$=lower alkyl) may be hydrolyzed with sodium hydroxide, potassium hydroxide or the like in an aqueous alcohol or in an anhydrous alcohol to give the alkali metal salt. Alternatively, the free acid ($R^2$=hydrogen) may be treated with an equimolar amount of sodium hydroxide, potassium hydroxide or the like preferably in an alcohol type solvent whereupon the corresponding alkali metal salt is obtained.

The compound (I) or salt thereof may be isolated/purified from the reaction mixture by conventional isolation/purification means, such as extraction, concentration, neutralization, filtration, recrystallization, column chromatography, thin layer chromatography, and the like.

The compounds (I) and pharmaceutically acceptable salts thereof of the present invention exhibit a strong serum lipid-lowering action and, because of their low toxicity, they can be used in the treatment or prevention of hyperlipemia and arteriosclerosis. As shown below, compounds (I) are effective in reducing serum cholesterol and triglycerides in animals.

The activity of representative compounds (I) of the invention was determined as follows:

(1) Reduction Of Serum TC In Rats Loaded With Cholesterol

Male rats (Wistar strain; 3 weeks of age) were fed for 7 days with a normal synthetic diet and classified in groups. A high-cholesterol diet containing 0.1% of the candidate compound was given to them for 3 days, then they were fasted overnight, blood was taken therefrom, and total cholesterol (TC) in the resulting serum was measured. The group to which the high-cholesterol diet containing no drug was fed was designated as the "control group" and that to which a normal synthetic diet was fed was named a "normal group". The control group contained 18 animals while the other groups had six animals. The inhibition of the increase of serum TC of the candidate compound was calculated by the following expression.

$$\text{Inhibition Of TC Increase} = \frac{(\text{Control } Gr) - (\text{Experimental } Gr)}{(\text{Control } Gr) - (\text{Normal } Gr)} \times 100$$

The results are given in Table 1.

TABLE 1

| Compound (Example Number) | TC Inhibition (%) | Compound (Example Number) | TC Inhibition (%) |
|---|---|---|---|
| 4 | 47** | 12 | 61** |
| 5 | 54** | 13 | 54** |
| 8 | 26** | 16 | 66** |
| 9 | 13* | 17 | 55** |

TABLE 1-continued

| Compound (Example Number) | TC Inhibition (%) | Compound (Example Number) | TC Inhibition (%) |
|---|---|---|---|
| 11 | 64** | Clofibrate | 31** |

* and ** mean that there was a significant difference with risks of 5% and 1%, respectively.

Thus it is seen that the compounds of the present invention are effective to reduce total serum cholesterol.

(2) Reduction Of Serum TC In Normal Rhesus Monkeys

Test Method: Male Rhesus monkeys (2 to 6 years age; 3.0 to 8.0 kg body weight) were used for the experiment. During the experiment, pellet chow (manufactured by Oriental Kobo KK) was given in an amount of 150 g once daily. Each group comprises 2 to 6 monkeys. The candidate compound was suspended in 0.5% carboxymethyl cellulose solution (for Experiment No. 1 and No. 2) or 0.5% methyl cellulose solution (for Experiment No. 3 and No. 4) and was given orally using a rubber tube at a dose of 30, 100 or 300 mg/kg for 10 days (Expt No. 3), for 14 days (Expt Nos. 1 and 2), or for 28 days (Expt. No. 4). Blood was taken out from the saphena veins of the hind leg one week before, immediately before, and 4, 7, 10, 14, 21 and 28 days after the administration of the compound and the serum TC was measured. The change in the serum TC was calculated by the following expression.

$$\text{Change In Serum } TC = \frac{(TC \text{ after administration}) - (TC \text{ before administration})}{(TC \text{ before administration})} \times 100$$

The term "TC before administration" means an average of the TC values of week and immediately before administration.

The results are given in Table 2.

TABLE 2

| Expt No | Compound Administered | Dose (mg/kg) | Nos Of Animals | Change In Serum TC (%) After | | | | | |
|---|---|---|---|---|---|---|---|---|---|
| | | | | 4 | 7 | 10 | 14 | 21 | 28 days |
| 1(1) | Control Group | — | 2 | | 6 | | −2 | | |
| (2) | Clofibrate | 100 | 3 | | −1 | | −5 | | |
| 2(1) | Control Group | — | 2 | | −1 | | −4 | | |
| (2) | Clofibrate | 300 | 2 | | −15 | | −13 | | |
| 3(1) | Control Group | — | 3 | −5 | −3 | −10 | | | |
| (2) | Example 4 | 300 | 3 | −15 | −24* | −23 | | | |
| (3) | Example 15 | 300 | 3 | −11 | −28 | −24 | | | |
| 4(1) | Control Group | — | 6 | | 10 | | | 1   1 | 1 |
| (2) | Example 4 | 30 | 5 | | −11* | | | −13**  −12** | −6 |
| (3) | Example 4 | 100 | 5 | | −19** | | | −31**  −31** | −26** |

* and ** mean that there is a significant difference within risks of 5% and 1%, respectively.

It is apparent that the compounds of the present invention are effective to reduce serum TC.

(3) Reduction Of Serum TC In Normal Beagles

Test Method: Male Beagles (8 to 18 months of age) were fed in separate cages with 300 g of pellet dog food once daily. The experimental groups for the tests comprised 3 to 6 Beagles. The compound to be tested was filled in gelatine capsules and 10 or 30 mg/kg was orally given for 28 days. Blood was taken from the middle veins in the forepaw at one week and immediately before administration and also 7, 14, 21 and 28 days after administration, and the serum TC and triglycerides (TG) were measured. The decrease in serum lipids was calculated by the following expressions.

$$\text{Change In Serum } TC = \frac{(TC \text{ after administration}) - (TC \text{ before administration})}{(TC \text{ before administration})} \times 100$$

(The term "TC before administration" is an average of the values of one week before and immediately before administration)

$$\text{Change In Serum } TG = \frac{(TG \text{ after administration}) - (TG \text{ before administration})}{(TG \text{ before administration})} \times 100$$

(The term "TG before administration" is an average of the values of one week before and immediately before administration)

The results are given in Table 3.

TABLE 3

| Expt Group | Change in Serum TC (%) after | | | |
|---|---|---|---|---|
| | 7 | 14 | 21 | 28 days |
| 1 | 1 ± 2 | −2 ± 4 | −8 ± 3 | −3 ± 3 |
| 2 | −4 ± 1 | −8 ± 3 | −10 ± 3 | −13 ± 2* |
| 3 | −17 ± 3** | −23 ± 2** | −23 ± 2 | −25 ± 3** |

| Expt Group | Change in Serum TG (%) after | | | |
|---|---|---|---|---|
| | 7 | 14 | 21 | 28 days |
| 1 | −3 ± 3 | 2 ± 6 | −10 ± 6 | −2 ± 5 |
| 2 | −26 ± 4** | −28 ± 4* | −31 ± 3 | −33 ± 3** |
| 3 | −24 ± 10 | −29 ± 5** | −31 ± 8 | −31 ± 3** |

* and ** mean that there is a significant difference within risks of 5% and 1%, respectively. The values are (average value ± standard error).

Experiment group 1 is a control group (6 Beagles), experiment group 2 is a group (3 Beagles) in which the compound of Example 4 was given at the dose of 10 mg/kg/day, and experiment group 3 is a group (6 Beagles) in which the compound of Example 4 was given at the dose of 30 mg/kg/day.

It is apparent that the present invention compound reduces serum TC and TG.

(4) Acute Toxicity (a) Experimental Method in Mice

DDY Strain male mice (6 weeks age) were fasted for 24 hours and used.

The test drug suspended in 0.5% methylcellulose in physiological saline was given orally, then normal feeding was continued, and the general symptoms of the mice were observed for two weeks. All of the compounds of the Examples showed low toxicity. No animal died after administration of 2 g/kg of the compounds.

(b) Experimental Method in Rats

SD-Strain male rats of 5 weeks age were used (one group comprised 4 rats). After giving the compound of Examples 4 and 15 orally, the general symptoms were observed for two weeks.

As a result, the rats receiving the compounds of Examples 4 and 15 showed no abnormalities after administration of 5 g/kg of the compounds.

The compounds (I) of the invention are used in the treatment and/or prevention of hyperlipemia and arteriosclerosis. In particular, compounds (I) are used to reduce serum lipids, such as serum cholesterol and serum triglycerides, in animals, including humans, by administering to an animal in need thereof an amount of compound (I) of the invention effective to reduce the serum cholesterol and/or serum triglycerides of said animal. Preferably, compound (I) will be administered in the form of a pharmaceutical composition, comprising an effective amount of the compound (I) in combination with a pharmaceutically acceptable, nontoxic, inert diluent or carrier, the carrier comprising one or more solid, semi-solid or liquid diluents, fillers and formulation adjuvants which are non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or fourth of a single dose. A single dose preferably contains an amount sufficient to produce the desired therapeutic effect upon administration at one application of one or more dosage units according to predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dosage for humans will be from about 100 to about 3000 mg, preferably from about 500 to about 1000 mg. In some instances, a sufficient therapeutic effect can be obtained at a lower dose, while in others a large dose will be required.

While the routes of administration of the compound (I) of the invention include oral, parenteral (i.e., intramuscular, intraperitoneal and intravenous), topical and rectal, oral administration is particularly preferred.

The preferred pharmaceutical compositions are therefore those in a form suitable for oral administration, such as tablets and liquids.

The present invention is further illustrated by referring to the following Reference Examples and Examples giving the manufacture of the present invention compounds.

REFERENCE EXAMPLE 1

(1)

N-[2-(4-Methoxycarbonylphenoxy)ethyl]phthalimide

Methyl 4-(2-Bromoethoxy)benzoate (126.52 g) and 99.5 g of potassium salt of phthalimide were dissolved in 600 ml of N,N-dimethylformamide and the solution was stirred at 78°–80° C. for 2 hours. The reaction solution was poured over ice water and extracted with chloroform. The chloroform layer was washed with water twice, dried with anhydrous magnesium sulphate, and concentrated in vacuo whereupon the residue was crystallised. Ether was added to the residue and filtered to give crystals in 149.23 g (yield: 94%). M.p. 129°–130.5° C.

(2) Methyl 4-(2-aminoethoxy)benzoate.

N-[2-(4-Methoxycarbonylphenoxy)ethyl]phthalimide (158.86 g) prepared in accordance with (1) and 73.33 g of hydrazine hydrate were dissolved in 1.5 liters of methanol and the solution was refluxed for 1 hour. The precipitate was removed by filtration and the filtrate was concentrated in vacuo. The residue was extracted with chloroform and washed with saturated sodium chloride solution twice. The organic solvent layer was dried with anhydrous magnesium sulphate and concentrated in vacuo. n-Hexane was added to the residue to make it crystallised followed by filtration to give 85.74 g of crystals (yield: 90%). M.p. 53°–55.5° C.

REFERENCE EXAMPLE 2

Methyl 4-(2-Aminoethoxy)benzoate

Methyl p-hydroxybenzoate (7.6 g) was dissolved in 50 ml of chloroform with heating, 2.15 g of aziridine was dropped in with stirring, and the mixture was heated to refluxed for 8 hours. The reaction solution was concentrated in vacuo and the residue was purified by a silica gel column chromatography (200 g of silica gel C-200; the eluting solvent used was a 9:1 mixture of chloroform and methanol).

The eluate was concentrated in vacuo and the residue was crystallized from n-hexane to give 4.9 g of desired product, m.p. 53°–55.5° C.

REFERENCE EXAMPLE 3

1-(4-Isopropylbenzoyl)aziridine

Aziridine (4.52 g) and 10.62 g of triethylamine were dissolved in 200 ml of benzene. p-Isopropylbenzoyl chloride (18.26 g) was dropped thereinto with stirring and keeping the inner temperature at 4° to 5° C. After the dropping, the mixture was stirred for 2 hours at the same temperature. After the reaction, the insoluble matters were removed by filtration, the filtrate was concentrated in vacuo, and the residue was purified by a silica gel column chromatography (300 g of silica gel C-200; the eluting solvent was chloroform) to give 17.70 g of the product, yield: 94%.

NMR ($^1$H-NMR CDCl$_3$ 60 MHz) δ ppm: 1.25 (6H, d), 2.36 (4H, s), 2.95 (1H, m), 7.23 (2H, d), 7.95 (2H, d).
IR (film) 1675 cm$^{-1}$.

EXAMPLE 1

Methyl 4-[2-(4-isopropylbenzamido)ethoxy]benzoate (1) Methyl 4-(2-aminoethoxy)benzoate (78 g) and 110.4 g of anhydrous potassium carbonate were added to 700 ml of chloroform and the mixture was stirred with cooling. p-Isopropylbenzoyl chloride (73 g) was dropped thereinto at 10° to 20° C. The mixture was then stirred for 3 hours. The reaction solution was washed with water. The chloroform layer was dried with anhydrous magnesium sulphate, concentrated in vacuo, the residue was crystallised with n-hexnae and the crystals were collected by filtration to give 116 g (yield: 85%) of desired crystals. M.p. 89°–91° C.

Elementary analysis calculated for $C_{20}H_{23}NO_4$: Calcd (%): C 70.36, H 6.79, N 4.10, Found (%): C 70.21, H 6.83, N 4.25.

(2) 1-(4-Isopropylbenzoyl)aziridine (1.89 g), 1.52 g of methyl p-hydroxybenzoate and 2.76 g of anhydrous potassium carbonate were added to 20 ml of N,N-dimethylformamide, the mixture was stirred at 59°–60° C. for 17 hours, the reaction solution was poured over ice water, the mixture was extracted with ethyl acetate, the extract was washed with 10% sodium hydroxide solution and then with water, dried with anhydrous magnesium sulfate, concentrated in vacuo, n-hexane was added to the residue, and the mixture was filtered to give 2.75 g (yield: 80.5%) of crystals, m.p. 89°–91° C.

Elementary Analysis for $C_{20}H_{23}NO_4$: Calcd (%): C 70.36, H 6.79, N 4.10, Found (%): C 70.25, H 6.68, N 4.08.

EXAMPLE 2

Methyl 4-[2-(4-tert-butylbenzamido)ethoxy]benzoate p-tert-Butylbenzoic acid (5.35 g) and 3.34 g of triethylamine were dissolved in 70 ml of chloroform and 3.26 g of ethyl chloroformate was dropped into the above mixture with stirring and cooling at 0° to 5° C. After the dropping, the mixture was stirred at the same temperature for 30 minutes and, after addition of 5.86 g of methyl 4-(2-aminoethoxy)benzoate thereto, the mixture was stirred for 6 hours more. The reaction solution was washed with 10% hydrochloric acid, saturated potassium carbonate solution, and water, dried with anhydrous magnesium sulpahte, concentrated in vacuo, and the residue was crystallised with n-hexane to give 9.8 g of crystals which were further recrystallised from ethyl acetate to give 7.64 g (yield: 71.65%) of the product, m.p. 112°–114° C.

Elementary analysis for $C_{21}H_{25}NO_4$: Calcd (%): C 70.95, H 7.09, N 3.94, Found (%): C 70.88, H 7.14, N 3.86.

EXAMPLE 3

Methyl 4-[2-(4-methylbenzamido)ethoxy]benzoate

Methyl 4-(2-aminoethoxy)benzoate (5.86 g) and 4.08 g of p-methylbenzoic acid were dissolved in 100 ml of N,N-dimethylformamide and then 6.19 g of N,N'-dicyclohexylcarbodiimide was gradually added thereto with stirring at room temperature.

After stirring for 10 hours, N,N'-dicyclohexylurea was removed by filtration, the filtrate was poured over into ice water, and the mixture was extracted with ethyl acetate. The organic layer was washed with 10% hydrochloric acid, saturated potassium carbonate solution, and water. Then it was dried with anhydrous magnesium sulphate, concentrated in vacuo, ether was added to the residue, the resulting crystals were collected by filtration, and 8.46 g of the crystals were recrystallised from ethyl acetate to give 6.83 g of crystalline product, m.p. 142°–144° C. Yield: 72.6%.

Elementary Analysis for $C_{18}H_{19}NO_4$: Calcd (%): C 68.97, H 6.11, N 4.47, Found (%): C 68.96, H 6.16, N 4.49.

EXAMPLE 4

4-[2-(4-Isopropylbenzamido)ethoxy]benzoic acid

Methyl 4-[2-(4-isopropylbenzamido)ethoxy]benzoate (102.42 g) was dissolved in 1 liter of ethanol with heating. A solution of 14.4 g of sodium hydroxide in 200 ml of water was added to the above ethanolic solution and the mixture was heated to reflux for 2 hours. The reaction solution was concentrated in vacuo, 1 liter of ice water was added to the residue, the mixture was neutralized with 10% hydrochloric acid, crystals separated out therefrom were collected by filtration, washed with water, dried and recrystallized from ethanol to give 80.5 g (yield: 82%) of crystalline product. M.p. 202°–203° C.

Elementary analysis for $C_{19}H_{21}NO_4$: Calcd (%): C 69.70, H 6.47, N 19.55, Found (%): C 69.71, H 6.33, N 19.38.

EXAMPLE 5

Sodium 4-[2-(4-isopropylbenzamido)ethoxy]benzoate

4-[2-(4-Isopropylbenzamido)ethoxy]benzoic acid (3.27 g) was dissolved in 50 ml of methanol, a solution of 0.40 g of sodium hydroxide in 5 ml of water was added thereto, the mixture was concentrated in vacuo, and crystallized residue was recrystallised from methanol to give 2.46 g of crystalline product, m.p. not lower than 300° C. IR $\gamma_{max}^{KBr}$ (cm$^{-1}$): 1640, 1605.

Elementary analysis for $C_{19}H_{20}NO_4Na.\frac{1}{2}H_2O$: Calcd (%): C 63.68, H 5.91, N 3.91, Found (%): C 63.44, H 5.77, N 3.88.

By the same operations as in Examples 1 to 5, the following compounds were prepared.

EXAMPLE 6

Methyl 4-(2-benzamidoethoxy)benzoate M.p. 111°–113° C.

Elementary analysis for $C_{17}H_{17}NO_4$: Calcd (%): C 68.22, H 5.72, N 4.68, Found (%): C 68.18, H 5.77, N 4.65.

EXAMPLE 7

4-(2-Benzamidoethoxy)benzoic acid

M.p. 207°–209.5° C.

Elementary analysis for $C_{16}H_{15}NO_4$: Calcd (%): C 67.36, H 5.30, N 4.91, Found (%): C 67.44, H 5.13, N 4.85.

EXAMPLE 8

4-[2-(4-Methylbenzamido)ethoxy]benzoic acid

M.p. 214°–216° C.

Elementary analysis for $C_{17}H_{17}NO_4$: Calcd (%): C 68.21, H 5.73, N 4.68, Found (%): C 68.31, H 5.64, N 4.63.

EXAMPLE 9

Ethyl 4-[2-(4-isopropylbenzamido)ethoxy]benzoate

M.p. 68°–71° C.

Elementary analysis for $C_{21}H_{25}NO_4$: Calcd (%): C 70.96, H 7.09, N 3.94, Found (%): C 70.74, H 7.18, N 4.00.

EXAMPLE 10

Ethyl 4-[2-(4-tert-butylbenzamido)ethoxy]benzoate

M.p. 77°–79° C.

Elementary analysis for $C_{22}H_{27}NO_4$: Calcd (%): C 71.52, H 7.37, N 3.79, Found (%): C 71.41, H 7.41, N 3.75.

EXAMPLE 11

4-[2-(4-tert-Butylbenzamido)ethoxy]benzoic acid

M.p. 206°–207° C.

Elementary analysis for $C_{20}H_{23}NO_4$: Calcd (%): C 70.36, H 6.79, N 4.10, Found (%): C 70.23, H 6.62, N 4.23.

EXAMPLE 12

Methyl 4-[2-(4-chlorobenzamido)ethoxy]benzoate

Methyl 4-(2-aminoethoxy)benzoate (19.5 g) and 13.8 g of anhydrous potassium carbonate were added to 200 ml of chloroform and the mixture was stirred with cooling. p-Chlorobenzoyl chloride (17.5 g) was dropped thereinto at 10°–20° C. The mixture was stirred for 3 hours. The reaction solution was washed with water, the chloroform layer was dried with anhydrous magnesium sulphate, concentrated in vacuo, the residue was crystallised with n-hexane, and the crystals were recrystallised with ethyl acetate/n-hexane to give 25.4 g of crystals of m.p. 125°–127° C., yield 76%.

Elementary analysis calculated afor $C_{17}H_{16}ClNO_4$: Calcd: C 61.18, H 4.83, N 4.20%, Found: C 61.34, H 4.80, N 4.24%.

EXAMPLE 13

Methyl 4-[2-(4-bromobenzamido)ethoxy]benzoate p-Bromobenzoic acid (6 g) and 3.35 g of triethylamine were dissolved in 80 ml of chloroform, the mixture was cooled at 0°–5° C. with stirring, and 3.26 g of ethyl chlorocarbonate was dropped thereinto. The mixture was stirred at the same temperature for 30 minutes, 5.86 g of methyl 4-(2-aminoethoxy)benzoate was added, and the mixture was stirred for 7 hours more. The reaction solution was washed with 10% hydrochloric acid, saturated potassium carbonate solution, and with water, dried with anhydrous magnesium sulphate, concentrated in vacuo, the residue was crystallised with n-hexane, and 8.5 g of crystals obtained were recrystallised from ethyl acetate to give 6.4 g of the product, m.p. 134°–136° C.

Elementary analysis for $C_{17}H_{16}BrNO_4$: Calcd (%): C 53.99, H 4.26, N 3.70, Found (%): C 53.98, H 4.04, N 3.72

EXAMPLE 14

Methyl 4-[2-(4-fluorobenzamido)ethoxy]benzoate

Methyl 4-(2-aminoethoxy)benzoate (19.5 g) and 14 g of p-fluorobenzoic acid were dissolved in 300 ml of N,N-dimethylformamide and 20.6 g of N,N'-dicyclohexylcarbodiimide was added thereto little by little with stirring at room temperature. The mixture was stirred for 8 hours, the resulting N,N'-dicyclohexylurea was removed by filtration, the filtrate was poured into ice water, and the mixture was extracted with ethyl acetate. The organic layer was washed with 10% hydrochloric acid, saturated potassium carbonate solution, and water. This was dried with anhydrous magnesium sulphate, concentrated in vacuo, the residue was crystallised with n-hexane, and the resulting 25.4 g of crystals were recrystallised from ethyl acetate/n-hexane to give 21.3 g (yield: 67%) of crystalline product. M.p. 105°–107° C.

Elementary analysis for $C_{17}H_{16}FNO_4$: Calcd (%): C 64.35, H 5.08, N 4.41, Found (%): C 64.41, H 5.14, N 4.47.

EXAMPLE 15

4-[2-(4-Chlorobenzamido)ethoxy]benzoic acid

Ten grams of methyl 4-[2-(4-chlorobenzamido)ethoxy]benzoate was dissolved in 100 ml of hot ethanol. A solution of 2.4 g of sodium hydroxide in 20 ml of water was added to the above ethanolic solution and the mixture was heated to reflux for 2 hours. The reaction solution was concentrated in vacuo, 100 ml of water was added to the residue, the mixture was neutralized with 10% hydrochloric acid, crystals separated out were collected by filtration, washed with water, dried and recrystallised from ethanol to give 8.4 g (yield: 87%) of crystalline product. M.p. 219°–220° C.

Elementary analysis for $C_{16}H_{14}ClNO_4$: Calcd (%): C 60.11, H 4.41, N 4.38, Found (%): C 60.23, H 4.28, N 4.32.

EXAMPLE 16

Sodium 4-[2-(4-chlorobenzamido)ethoxy]benzoate

4-[2-(4-Chlorobenzamido)ethoxy]benzoic acid (3.19 g) was dissolved in 50 ml of methanol. A solution of 0.40 g of sodium hydroxide in 5 ml of water was added to the above methanolic solution, the mixture was concentrated in vacuo, the crystallised residue was recrystallised from methanol, and 2.30 g of crystalline product was obtained. M.p. not lower than 300° C.

IR $\gamma_{max}^{KBr}$ (cm$^{-1}$): 1640, 1605.

Elementary analysis for $C_{16}H_{13}ClNO_4Na.\frac{1}{2}H_2O$: Calcd (%): C 54.79, H 4.02, N 3.99, Found (%): C 54.83, H 4.15, N 4.01.

Similarly were prepared the following compounds as in Examples 12 to 16.

EXAMPLE 17

4-[2-(4-Bromobenzamido)ethoxy]benzoic acid

M.P. 233°–235° C.

Elementary analysis for $C_{16}H_{14}BrNO_4$: Calcd (%): C 52.77, H 3.86, N 3.85, Found (%): C 52.82, H 3.80, N 3.84.

EXAMPLE 18

4-[2-(4-Fluorobenzamido)ethoxy]benzoic acid

M.p. 196°–198° C.

Elementary analysis for $C_{16}H_{14}FNO_3$: Calcd (%): C 63.36, H 4.65, N 4.62, Found (%): C 63.14, H 4.84, N 4.67.

EXAMPLE 19

Ethyl 4-[2-(4-chlorobenzamido)ethoxy]benzoate

M.p. 163°–137° C.

Elementary analysis for $C_{18}H_{18}ClNO_4$: Calcd (%): C 62.16, H 5.22, N 4.03, Found (%): C 62.15, H 5.15, N 4.04.

EXAMPLE 20

Ethyl 4-[2-(4-fluyorobenzamido)ethoxy]benzoate

M.p. 111°–112° C.

Elementary analysis for $C_{18}H_{18}FNO_4$: Calcd (%): C 65.25, H 5.48, N 4.23, Found (%): C 65.30, H 5.68, N. 4.19.

(Effect)

It is apparent from the above results that the present invention compound (I) are novel and exhibit strong hypolipemic action when given to human being and animals with markedly low toxicity. Accordingly they are useful as remedies for arteriosclerosis and hyperlipemia with high TC and TG in blood.

We claim:

1. A compound of formula (I)

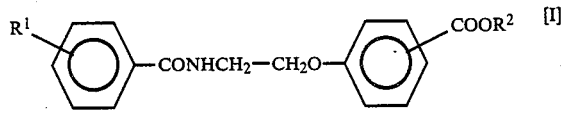

or a pharmaceutically acceptable salt thereof, wherein $R^1$ is hydrogen, halogen or alkyl of from about 1 to about 7 carbon atoms and $R^2$ is hydrogen or alkyl of from about 1 to about 7 carbon atoms.

2. The compound according to claim 1, wherein said alkyl has from about 1 to about 4 carbon atoms.

3. The compound according to claim 1, wherein said halogen is fluorine, chlorine, bromine or iodine.

4. The compound according to claim 1, which is 4-[2-(4-isopropylbenzamido)ethoxy]benzoic acid or a pharmaceutically acceptable salt thereof.

5. The compound according to claim 4, wherein said salt is the sodium salt.

6. A method of reducing serum lipids in animals, including humans, which comprises administering to an animal in need thereof an amount of the compound of claim 1 effective to reduce the serum lipids of said animal.

7. A method of reducing serum cholesterol and/or serum triglycerides in animals, including humans, which comprises administering to an animal in need thereof an amount of the compound of claim 1 effective to reduce the serum cholesterol and/or serum triglycerides of said animal.

8. A pharmaceutical composition for reducing serum lipids in animals, including humans, which comprises an amount of the compound of claim 1 effective to reduce the serum lipids of said animal in combination with a pharmaceutically acceptable carrier or diluent therefor.

9. A pharmaceutical composition for reducing serum cholesterol and/or serum triglycerides in animals, including humans, which comprises an amount of the compound of claim 1 effective to reduce the serum cholesterol and/or serum triglycerides of said animal in combination with a pharmaceutically acceptable carrier or diluent therefor.

* * * * *